US006933277B2

(12) United States Patent
Brenneman et al.

(10) Patent No.: US 6,933,277 B2
(45) Date of Patent: Aug. 23, 2005

(54) PREVENTION OF FETAL ALCOHOL SYNDROME AND NEURONAL CELL DEATH WITH ADNF POLYPEPTIDES

(75) Inventors: Douglas E. Brenneman, Damascus, MD (US); Catherine Y. Spong, Arlington, VA (US); Illana Gozes, Ramat Hasharon (IL); Merav Bassan, Natania (IL); Rachel Zamostiano, Hod Hashron (IL)

(73) Assignees: The United States of America as represented by the Department of Health and Human Services, Washington, DC (US); Ramot University Authority for Applied Research and Industrial Development, Ltd., Tel Aviv (IL)

( * ) Notice: Subject to any disclaimer, the term of this patent is extended or adjusted under 35 U.S.C. 154(b) by 0 days.

(21) Appl. No.: 09/267,511

(22) Filed: Mar. 12, 1999

(65) Prior Publication Data

US 2002/0111301 A1 Aug. 15, 2002

(51) Int. Cl.$^7$ ........................ A61K 38/00; A61K 39/00; A61K 38/24; A01N 37/18; C07K 1/00
(52) U.S. Cl. ........................ 514/12; 514/2; 424/184.1; 424/185.1; 424/198.1; 530/350; 530/399
(58) Field of Search ............................... 514/12–16, 2, 514/44; 424/185.1, 198.1; 530/350, 399, 300

(56) References Cited

U.S. PATENT DOCUMENTS 5,767,240 A  6/1998  Brenneman et al. ........ 530/350

FOREIGN PATENT DOCUMENTS

| WO | WO 92/18140 | 10/1992 | .......... A61K/37/00 |
|----|-------------|---------|----------------------|
| WO | WO 96/11948 | 4/1996  | .......... C07K/14/475 |
| WO | WO 98/35042 | 8/1998  | ........... C12N/15/18 |

OTHER PUBLICATIONS

Hannigan et al., Neurotoxicol. & Teratol., 22(1):103–11, 2000.*
Skolnick et al., Trends in Biotech. 18(1):34–39, 2000.*
Smith AE., Ann. Rev. of Microbiol., 49:807–38, 1995.*
Mahato et al., J. of Drug Targeting, 4(6):337–57, 1997.*
Spong et al., Prevention of fetal demise and growth restriction in a mouse model of fetal alcohol syndrome. *J Pharmacol Exp Ther.*;297(2):774–9 (2001).
Wilkemeyer et al., Differential effects of ethanol antagonism and neuroprotection in peptide fragment NAPVSIPQ prevention of ethanol-induced developmental toxicity *PNAS* 100: 8543–8548 (2003).
Spong et al., "Prevention of Fetal Alcohol Syndrome by Novel Peptides", *FASEB JOURNAL*, 13:(5) part 2, p. A881 XP–002148904, (Mar. 15, 1999).

Spinney L., "New Peptides prevent brain damage 'news!'", *Molecular Medicine Today* 5:(7)282 (Jul. 1999).
Oberdoester, J. et al., "The Effects of ethanol on neuronal cell death: Implication for the fetal alcohol syndrome", *FASEB Journal*, 12:4 A134 (Mar. 17, 1998).
Bassan, M. et al. "VIP–Induced Mechanism of Neuroprotection: The Complete Sequence of a Femtomolar–Acting Activity–Dependent Neuroprotective Protein." *Regulatory Peptides*, 71(2):, Aug. 15, 1997.
Bassan, M. et al. "Complete Sequence of a Novel Protein-Containing a Femtomolar–Activity–Dependent Neuroprotective Peptide." *Journal of Neurochemistry* 72:1283–1293 (1999).
Beni–Adani, L. et al. "Activity–Dependent Neurotrophic Protein is Neuroprotective in a Mouse Model of Closed Head Injury." Society for Neuroscience, 28$^{th}$ Annual Meeting, Los Angeles, CA, Nov. 7–12, 1998. *Abstracts* 23(1):1043 (1998).
Brenneman, D.C. and Gozes, I. "A Femtomolar–Acting Neuroprotective Peptide." *Journal of Clinical Investigation* 97:229–230 (1996).
Brenneman, D.E. et al. "Identification of a Nine Amino Acid Core Peptide from Activity Dependent Neurotrophic Factor I." Society for Neuroscience, 27$^{th}$ Annual Meeting, New Orleans, LA, Oct. 25–30, 1997. *Abstracts* 23(2): 2250 (1997).
Brenneman, D.E. et al. "Activity–Dependent neutotrophic Factor: Structure–Activity Relationships of Femtomolar–Acting Peptides." *Journal of Pharmacology and Experimental Therapeutics* 285: 619–627 (1998).
Davidson, A. et al. "Protection Against Developmental Retardation and Learning Impairments in Apolipoprotein E–Deficient Mice by Activity–Dependent Femtomolar–Acting Peptides." Society for Neuroscience, 27$^{th}$ Annual Meeting, New Orleans, LA, Oct. 25–30, 1997. *Abstracts* 23(2)2250 (1997).
Dibbern, D.A., Jr. et al. "Inhibition of Murine Embryonic Growth by Human Immunodeficiency Virus Envelope Protein and Its Prevention by Vasoactive Intestinal Peptide and Activity–Dependent Neurotrophic Factor." *Journal of Clinical Investigation* 99: 2837–2841 (1997).

(Continued)

*Primary Examiner*—Olga N. Chernyshev
(74) *Attorney, Agent, or Firm*—Townsend and Townsend and Crew LLP

(57) ABSTRACT

This invention relates to a method for reducing a condition associated with fetal alcohol syndrome in a subject who is exposed to alcohol in utero with an ADNF polypeptide. In particular, the present invention relates to a method of reducing a condition associated with fetal alcohol syndrome in a subject who is exposed to alcohol in utero with a combination of ADNF I and ADNF III polypeptides. The present invention further relates to a method for reducing neuronal cell death by contacting neuronal cells with a combination of ADNF I and ADNF III polypeptides. Still further, the present invention relates to a pharmaceutical composition comprising a combination of ADNF I and ADNF III polypeptides.

16 Claims, 4 Drawing Sheets

OTHER PUBLICATIONS

Giladi, E. "Protection Against Developmental and Learning Impairments in Apolipoprotein E–Deficient Mice by Activity–Dependent Femtomolar–Acting Peptides." *Neuroscience Letters* Supplement 48 S1–S60, P. S19 (1997).

Glazner, G.W. et al. "A 9 Amino Acid Peptide Fragment of Activity–Dependent Neurotrophic Factor (ADNF) Protects Neurons from Oxidative Stress–Induced Death." Society for Neuroscience, 27th Annual Meeting, New Orleans, LA, Oct. 25–30, 1997. *Abstracts* 23(2)2249 (1997).

Gozes, I. et al. "Stearyl–Norleucine–Vasoactive intestinal Peptide (VIP): A novel VIP Analog for Noninvasive Impotence Treatment." *Endocrinology* 134: 2125 (1994).

Gozes, I. et al. "Superactive Lipophilic Peptides Discriminate Multiple Vasoactive intestinal Peptide Receptors." *Journal of Pharmacology and Experimental Therapeutics* 27:3161–167 (1995).

Gozes, I. et al. "Neuroprotective Strategy for Alzheimer Disease: Intranasal Administration of a Fatty Neuropeptide." *Proc. Natl. Acad. Sci. USA* 93:427–432 (1996).

Gozes, I. and Brenneman, D.E. "Activity–Dependent Neurotrophic Factor (ADNF)." *Journal of Molecular Neuroscience* 7:235–244 (1996).

Gozes, I. et al. "Protection Against Developmental Retardation in Apolipoprotein E–Deficient Mice by a Fatty neuropeptide: Implications for Early Treatment of Alzheimer's Disease." *Journal of Neurobiology* 33:329–342 (1997).

Gozes I. et al. "Antiserum to Activity–Dependent Neurotrophic Factor Produces Neuronal Cell Death in CNS Cultures: Immunological and Biological Specificity." *Developmental Brain Research* 99:167–175 (1997).

Gozes, I. et al. "The cDNA Structure of a Novel Femtomolar–Acting Neuroprotective Protein: Activity–Dependent–Neurotrophic Factor III (ADNFIII)." Society for Neuroscience, 27th Annual Meeting, New Orleans, LA, Oct. 25–30, 1997. *Abstracts* 23(2):2250 (1997).

Gozes, I. et al. A Femtomolar–Acting Activity–Dependent Neuroprotective Protein (ADNP). *Neuroscience Letters* Supplement 48 S1–S60, p. S21 (1997).

Hill, J.M. et al. "Learning Impairment in Adult Mice Produced by Early Embryonic Administration of Antiseum to Activity–Dependent Neurotrophic Factor (ADNF)." Society for Neuroscience, 27th Annual Meeting, New Orleans, LA, Oct. 25–30, 1997. *Abstracts* 23(2):2250 (1997).

Lilling, G. et al. "Inhibition of Human Neuroblastoma Growth by a Specific VIP Antagonist." *Journal of Molecular Neuroscience* 5: 231–239 (1995).

McKune, S.K. et al. "Localization of mRNA for Activity–Dependent Neurotrophic Factor III (ADNF III) in mouse Embryo and Adult CNS." Society for Neuroscience, 27th Annual Meeting, New Orleans, LA, Oct. 25–30, 1997. *Abstracts* 23(2):2249 (1997).

Nelbock, P. et al. A cDNA for a Protein that Interacts with the Human Immunodeficiency Virus Tat Transactivator. *Science*, 248:1650–1653 (1990).

Pelsman, A. et al. "In Vitro Degeneration of Down Syndrome neurons is Prevented by Activity–Dependent Neurotrophic Factor–Derived Peptides." Society for Neuroscience, 28TH Annual Meeting, Los Angeles, CA, Nov. 7–12, 1998. *Abstracts* 24:1044 (1998).

Brenneman et al. "Neuronal Cell Killing by the Envelope Protein of HIV and Its Prevention by Vasoactive Intestinal Peptide." *Nature* 335:636 (1988).

Brenneman et al. "N–Methyl–D–Aspartate Receptors Influence Neuronal Survival in Developing Spinal Cord Cultures" *Dev. Brain Res.* 51:63 (1990).

Glazner, G.W. et al. "Activity Dependent Neurotrophic Factor: A Potent Regulator of Embryonic Growth." *Anat. Embryol.* 200:65–71 (1999).

Gressens, P. et al. "Growth factor function of vasoactive intestinal peptide in whole cultured mouse embryos." *Nature*, 362:155–58 (1993).

* cited by examiner

* P ≤0.02 vs alcohol

PREVENTION OF FETAL ALCOHOL SYNDROME AND NEURONAL CELL DEATH WITH ADNF POLYPEPTIDES

CROSS-REFERENCES TO RELATED APPLICATIONS

This application is related to U.S. Ser. No. 07/871,973 filed Apr. 22, 1992, now U.S. Pat. No. 5,767,240, issued Jun. 16, 1998; U.S. Ser. No. 08/342,297, filed Oct. 17, 1994 (published as WO96/11948); U.S. Ser. No. 60/037,404, filed Feb. 27, 1997 (published as WO98/35042); and U.S. Ser. No. 09/187,330, filed Nov. 11, 1998. All of these applications are incorporated herein by reference.

STATEMENT AS TO RIGHTS TO INVENTIONS MADE UNDER FEDERALLY SPONSORED RESEARCH AND DEVELOPMENT

Not applicable.

FIELD OF THE INVENTION

This invention relates to a method for reducing a condition associated with fetal alcohol syndrome in a subject who is exposed to alcohol in utero with an ADNF polypeptide. In particular, the present invention relates to a method for reducing a condition associated with fetal alcohol syndrome in a subject who is exposed to alcohol in utero with a combination of ADNF I and ADNF III polypeptides. The present invention further relates to a method for reducing neuronal cell death by contacting neuronal cells with a combination of ADNF I and ADNF III polypeptides. Still further, the present invention relates to a pharmaceutical composition comprising a combination of ADNF I and ADNF III polypeptides.

BACKGROUND OF THE INVENTION

In the United States, fetal alcohol syndrome (FAS) affects 12,000 babies each year and the rate of frequent drinking during pregnancy has increased four-fold between 1991 and 1995 (*MMWR* 46:346–50 (1997)). Maternal alcohol consumption is the most commonly identifiable non-genetic cause of mental retardation. In addition, consuming over 3 drinks per week in the first trimester has been shown to double the risk of miscarriage (Windham et al., *Epidemiology,* 8:509–14 (1997)). An increase in free radical formation has been implicated in the pathogenesis of alcohol-induced central nervous system dysfunction in FAS. Ethanol treatment in cell culture depresses cell viability and generates reactive oxygen intermediates including superoxide, hydrogen peroxide and hydroxyl anions (Guerri et al., *Free Radicals in Diagnostic Medicine*, Plenum Press, New York, 291–305 (1994)). Acute alcohol exposure has been shown to increase superoxide generation and decrease extraperoxisomal catalase activity, decreasing Cu, Zn-superoxide dismutase activity (Nordmann et al., *Free Radical Biology and Medicine* 12:219–40 (1992)).

The most devastating effects of alcohol exposure occur during organogenesis and development of the nervous system (Armant et al., *Sem. Perinatol.,* 20:127–39 (1996)), during the time when vasoactive intestinal peptide (VIP) has been shown to regulate mouse embryonic growth (Gressens et al., *Nature,* 362:155–8 (1993)). There are known interactions between alcohol and VIP, a neuropeptide that is a regulator of early postimplantation mouse embryonic growth (Gressens et al., *J. Clin. Invest.* 94:2020–2027 (1994)). In pregnant mice, both alcohol and VIP antagonist treatment may result in some of the features of FAS, including fetal growth restriction and microcephaly. Interactions between alcohol and VIP include a decrease in VIP mRNA in the suprachiasmatic nucleus with alcohol exposure (Maderia et al., *J. Neurosci.,* 17:1302–19 (1997)), and a decrease in VIP binding in rat enterocytes after chronic alcohol consumption (Jimenez et al., *Gen. Pharmac.,* 23:607–11 (1992)). Ethanol has also been shown to result in cell death in the neuroepithelium (Gressens et al., *Alc. & Alc.,* 27:219–26 (1992)), which is a prominent site of VIP binding (Hill et al., *J. Comp. Neurol.,* 342:186–205 (1994)).

For individuals who were exposed to alcohol in utero, they may suffer from various mental and physical defects associated with fetal alcohol syndrome. For example, they may suffer from growth retardations; physical, mental, and behavioral abnormalities; central nervous system impairment, including developmental delay, small head size, and speech or language delay; and facial abnormalities.

In view of its severe and lifelong impact on the fetus, fetal alcohol syndrome is a major public concern. Although educating the public, in particular pregnant women, regarding consumption of alcohol and its effect on the fetus and refraining from drinking during pregnancy are the obvious, sensible approach to resolving this problem, this approach alone has not been effective as illustrated by the alarming statistics set forth above. Another method which can be used in conjunction with educating the public is approaching this problem clinically, i.e., intervening against alcohol induced damage by treating pregnant women with prophylactic compounds. Therefore, there is a need to identify and isolate compounds which can reduce fetal alcohol syndrome. The identification and isolation of new compounds would allow aid in the reduction and prevention of fetal alcohol syndrome and other related medical conditions.

SUMMARY OF THE INVENTION

The present invention provides for the first time a method for reducing a condition associated with fetal alcohol syndrome in a subject who is exposed to alcohol in utero using ADNF polypeptides. The present invention further provides a method for reducing neuronal cell death using a combination of ADNF I and ADNF III polypeptides. Still further, the present invention provides a pharmaceutical composition comprising a combination of ADNF I and ADNF III polypeptides.

The ADNF polypeptides include ADNF I and ADNF III polypeptides and subsequences thereof which contain their respective active sites and provide neuroprotective and growth-promoting functions. The ADNF I polypeptides have an active site comprising the following amino acid sequence: Ser-Ala-Leu-Leu-Arg-Ser-Ile-Pro-Ala ("SALLRSIPA"; SEQ ID NO:1). The ADNF III polypeptides also have an active site comprising a few amino acid residues, namely, the following amino acid sequence: Asn-Ala-Pro-Val-Ser-Ile-Pro-Gln ("NAPVSIPQ"; SEQ ID NO:2). These ADNF polypeptides have previously been shown each on their own to have remarkable potency and activity in animal models related to neurodegeneration, and but have not been shown to reduce or prevent a condition associated with fetal alcohol syndrome.

As such, in one aspect, the present invention provides a method for reducing a condition associated with fetal alcohol syndrome in a subject who is exposed to alcohol in utero, the method comprising administering to the subject an ADNF polypeptide in an amount sufficient to reduce the condition associated with fetal alcohol syndrome. Such conditions include, for example, a decreased body weight, a decreased brain weight, a decreased VIP mRNA, and death of the subject in utero.

In one embodiment, an ADNF polypeptide is selected from the group consisting of a full length ADNF I polypeptide, a full length ADNF III polypeptide, and a combination of a full length ADNF I polypeptide and a full length ADNF III polypeptide.

In another embodiment, the ADNF polypeptide is a member selected from the group consisting of: (a) an ADNF I polypeptide having the following amino acid sequence: $(R^1)_x$-Ser-Ala-Leu-Leu-Arg-Ser-Ile-Pro-Ala-$(R^2)_y$ (SEQ ID NO:3); (b) an ADNF III polypeptide having the following amino acid sequence: $(R^3)_w$-Asn-Ala-Pro-Val-Ser-Ile-Pro-Gln-$(R^4)_z$ (SEQ ID NO:4); and (c) a combination of the ADNF I polypeptide of part (a) and the ADNF III polypeptide of part (b); wherein $R^1$, $R^2$, $R^3$, and $R^4$ are independently selected and are an amino acid sequence comprising from 1 to about 40 amino acids, wherein each amino acid is independently selected; and x, y, w, and z are independently selected and are equal to zero or one. In yet another embodiment, at least one of the ADNF polypeptide is encoded by a nucleic acid.

In another aspect, the present invention provides a method for reducing neuronal cell death, the method comprising contacting a neuronal cell with a combination of an ADNF I polypeptide and an ADNF III polypeptide in an amount sufficient to reduce neuronal cell death.

In one embodiment, the ADNF polypeptide used to reduce neuronal cell death is a combination of a full length ADNF I polypeptide and a full length ADNF III polypeptide. In another embodiment, (a) the ADNF I polypeptide has the following amino acid sequence: $(R^1)_x$-Ser-Ala-Leu-Leu-Arg-Ser-Ile-Pro-Ala-$(R^2)_y$ (SEQ ID NO:3); and (b) the ADNF III polypeptide has the following amino acid sequence: $(R^3)_w$-Asn-Ala-Pro-Val-Ser-Ile-Pro-Gln-$(R^4)_z$ (SEQ ID NO:4); wherein $R^1$, $R^2$, $R^3$, and $R^4$ are independently selected and are an amino acid sequence comprising from 1 to about 40 amino acids wherein each amino acid is independently selected; and x, y, w, and z are independently selected and are equal to zero or one.

In another aspect, the present invention provides a pharmaceutical composition comprising a pharmaceutically acceptable excipient and a combination of an ADNF I polypeptide and an ADNF III polypeptide.

In one embodiment, the pharmaceutical composition comprises a pharmaceutically acceptable excipient and a combination of a full length ADNF I polypeptide and a full length ADNF III polypeptide. In another embodiment, the pharmaceutical composition comprises: (a) an ADNF I polypeptide having the following amino acid sequence: $(R^1)_x$-Ser-Ala-Leu-Leu-Arg-Ser-Ile-Pro-Ala-$(R^2)_y$ (SEQ ID NO:3); and (b) an ADNF III polypeptide having the following amino acid sequence: $(R^3)_w$-Asn-Ala-Pro-Val-Ser-Ile-Pro-Gln-$(R^4)_z$ (SEQ ID NO:4); wherein $R^1$, $R^2$, $R^3$, and $R^4$ are independently selected and are an amino acid sequence comprising from 1 to about 40 amino acids, wherein each amino acid is independently selected; and x, y, w, and z are independently selected and are equal to zero or one.

Figure 1:
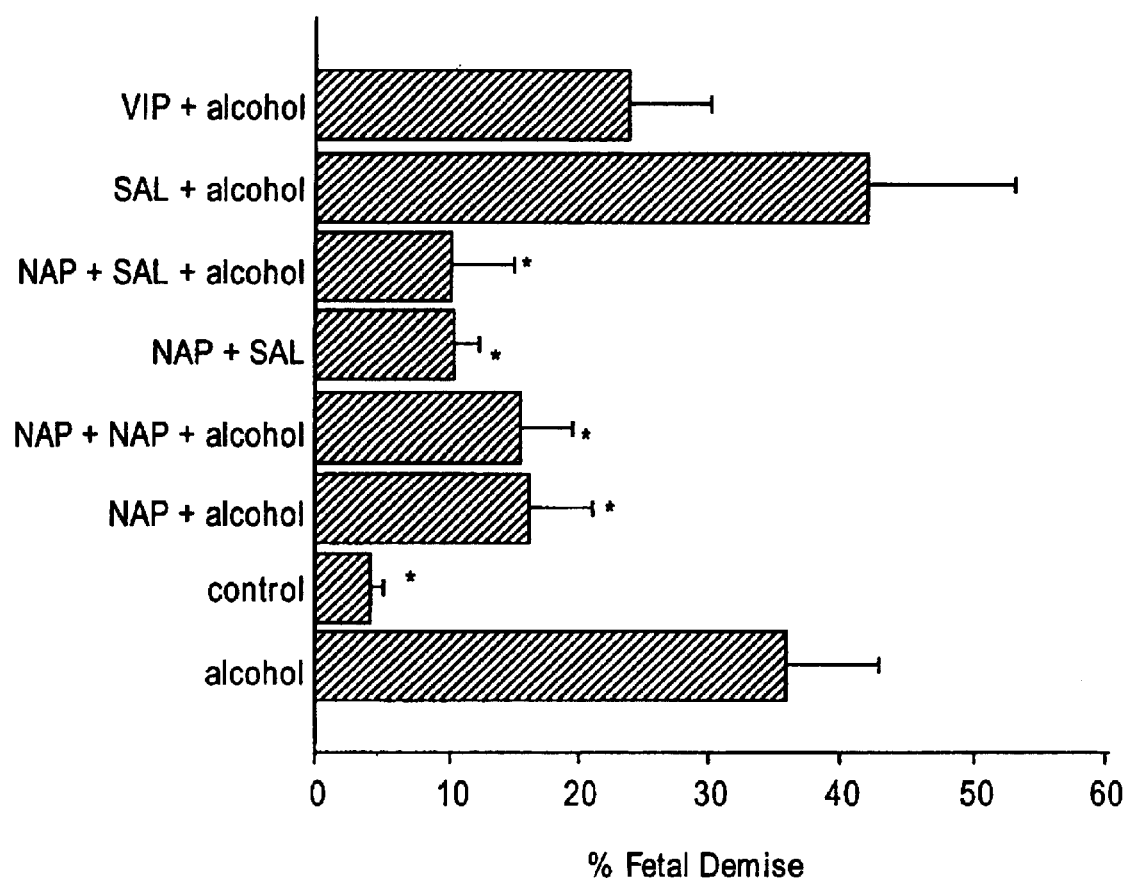
FIG. 1 illustrates the effects of pretreatment with ADNF polypeptides on fetal demise. At E18, the number of living and demised embryos was counted and the percentage of demises was calculated. Treatment with alcohol was given on E8, pretreatment with peptides given 30 minutes prior. Comparisons are made to the alcohol group, overall ANOVA p<0.001. Post-hoc Fishers tests were performed, with the * groups significantly different than the alcohol group (all post-hoc p≦0.01). Sample size (n) was control (33), alcohol (35), NAPVSIPQ (SEQ ID NO:2)+alcohol (25), NAPVSIPQ (SEQ ID NO:2)+NAPVSIPQ (SEQ ID NO:2)+ alcohol, (17), SALLRSIPA (SEQ ID NO:1)+alcohol (15), VIP+alcohol (18), NAPVSIPQ (SEQ ID NO:2)+ SALLRSIPA (SEQ ID NO:1)+alcohol (20), and NAPVSIPQ (SEQ ID NO:2)+SALLRSIPA (SEQ ID NO:1) alone (19).

In all the figure legends, a peptide having an amino acid sequence of SALLRSIPA (SEQ ID NO:1) is referred to as "SAL," and a peptide having a sequence of NAPVSIPQ (SEQ ID NO:2) is referred to as "NAP."

DEFINITIONS

The phrase "ADNF polypeptide" refers to one or more activity dependent neurotrophic factors (ADNF) that have an active site comprising the amino acid sequence of SALL-RSIPA (SEQ ID NO:1) or NAPVSIPQ (SEQ ID NO:2), or conservatively modified variants thereof that have neurotrophic/neuroprotective activity as measured with in vitro cortical neuron culture assays described by, e.g., Hill et al., *Brain Res.* 603, 222–233 (1993); Venner & Gupta, *Nucleic Acid Res.* 18, 5309 (1990); and Peralta et al., *Nucleic Acid Res.* 18, 7162 (1990); Brenneman et al., *Nature* 335, 636 (1988); or Brenneman et al., *Dev. Brain Res.* 51:63 (1990); Forsythe & Westbrook, *J. Physiol. Lond.* 396:515 (1988). An ADNF polypeptide can be an ADNF I polypeptide, an ADNF III polypeptide, their alleles, polymorphic variants, or interspecies homolog, or any subsequences thereof that exhibit neuroprotective/neurotrophic action on, e.g., neurons originating in the central nervous system either in vitro or in vivo.

The term "ADNF I" refers to an activity dependent neurotrophic factor polypeptide having a molecular weight of about 14,000 Daltons with a pI of 8.3±0.25. As described above, ADNF I polypeptides have an active site comprising an amino acid sequence of Ser-Ala-Leu-Leu-Arg-Ser-Ile-Pro-Ala (also referred to as "SALLRSIPA"; SEQ ID NO:1). See, Brenneman et al., *J. Clin. Invest.*, 97:2299–2307 (1996), Glazner et al., *Anat Embryol* (In press), Brenneman et al., *J. Pharm. Exp. Ther.*, 285:619–27 (1998), Gozes & Brenneman, *J. Mol. Neurosci.* 7:235–244 (1996), and Gozes et al., *Dev. Brain Res.* 99:167–175 (1997), all of which are herein incorporated by reference.

The terms "ADNF III" and "ADNP" refer to an activity dependent neurotrophic factor polypeptide having a predicted molecular weight of about 95 kDa (about 828 amino acid residues) and a pI of about 5.99. As described above, ADNF III polypeptides have an active site comprising an amino acid sequence of Asn-Ala-Pro-Val-Ser-Ile-Pro-Gln (also referred to as "NAPVSIPQ"; SEQ ID NO:2). See, Bassan et al., *J. Neurochem.* 72:1283–1293 (1999), incorporated herein by reference.

The phrases "fetal alcohol syndrome" and "fetal alcohol effects" relate to various physical and mental conditions of an embryo, a fetus, or a subject who is exposed to alcohol in utero (e.g., whose mother consumed alcohol during pregnancy) in an amount sufficient to initiate the development of these conditions or to cause these conditions in the absence of prevention treatment, e.g., treatment with ADNF polypeptides. Some of these conditions include, but are not limited to, the following:

skeletal deformities: deformed ribs and sternum; curved spine; hip dislocations; bent, fused, webbed, or missing fingers or toes; limited movement of joints; small head;

facial abnormalities: small eye openings; skin webbing between eyes and base of nose; drooping eyelids; nearsightedness; failure of eyes to move in same direction; short upturned nose; sunken nasal bridge; flat or absent groove between nose and upper lip; thin upper lip; opening in roof of mouth; small jaw; low-set or poorly formed ears;

organ deformities: heart defects; heart murmurs; genital malformations; kidney and urinary defects;

central nervous system handicaps: small brain; faulty arrangement of brain cells and connective tissue; mental retardation—usually mild to moderate, but occasionally severe; learning disabilities; short attention span; irritability in infancy; hyperactivity in childhood; poor body, hand, and finger coordination (see, e.g., www.well.com/user/woa/fsfas.htm); and other abnormalities: brain weight reduction, body weight reduction, a higher rate of death in utero, and a decrease in the level of VIP (e.g., VIP mRNA).

The phrase "reducing a condition associated with fetal alcohol syndrome" refers to reduction, including prevention, of parameters associated with fetal alcohol syndrome. Reduction is a change of a parameter by about 10% to about 100%, preferably at least about 50%, and more preferably at least about 80% compared to that of the control (e.g., exposed to alcohol in utero without any treatment, e.g., treatment with ADNF polypeptides). The parameters can be any physical or mental conditions listed above. For example, they can be: (1) a reduction in the percentage of fetus death, (2) a reduction in fetal weights and fetal brain weights, or (3) a reduction in the level of VIP (e.g., VIP mRNA) in embryos.

The phrase "a subject with fetal alcohol syndrome" relates to an embryo, a fetus, or a subject, in particular a human, who is exposed to alcohol in utero and who has fetal alcohol syndrome or who is in danger of developing due to maternal alcohol consumption any of the conditions related to fetal alcohol syndrome, such as the effects described above.

The phrase "reducing neuronal cell death" refers to reduction, including prevention, of neuronal cell death. Reduction is a change of a parameter by about 10% to about 100%, preferably at least about 50%, and more preferably at least about 80% compared to that of the control (e.g., without treatment with, e.g., ADNF polypeptides). The reduction of neuronal cell death can be measured by any methods known in the art. For example, a combination of ADNF I and ADNF III polypeptides that reduce neuronal cell death can be screened using the various methods described in U.S. Ser. No. 60/037,404, filed Feb. 27, 1997 (published as WO98/35042) and U.S. Ser. No. 09/187,330, filed Nov. 6, 1998, incorporated herein by reference. In addition, the assays described in the following references can also be used: Hill et al., *Brain Res.* 603, 222–233 (1993); Venner & Gupta, *Nucleic Acid Res.* 18, 5309 (1990); Peralta et al., *Nucleic Acid Res.* 18, 7162 (1990); Brenneman et al., *Nature* 335, 636 (1988); and Brenneman et al., *Dev. Brain Res.* 51:63 (1990); Forsythe & Westbrook, *J. Physiol. Lond.* 396:515 (1988). The teachings of these publications are hereby incorporated in their entirety by reference.

The term "contacting" is used herein interchangeably with the following: combined with, added to, mixed with, passed over, incubated with, flowed over, etc. Moreover, the ADNF polypeptides or nucleic acids encoding them of the present invention can be "administered" by any conventional method such as, for example, parenteral, oral, topical, and inhalation routes. In presently preferred embodiments, parenteral and nasal inhalation routes are employed. In the context of methods related to fetal alcohol syndrome, ADNF polypeptides can be administered directly to an embryo, a fetus, or a subject in utero or to the subject in utero indirectly, by administering the polypeptide to the mother by any other methods described herein.

"An amount sufficient" or "an effective amount" is that amount of a given ADNF polypeptide that reduces the neuronal cell death of interest or reduces fetal alcohol syndrome as described herein. For example, in the context of reducing fetal alcohol syndrome, "an amount sufficient" or "an effective amount" is that amount of a given ADNF polypeptide that reduces or prevents, for example, (1) the percentage of fetus death, (2) a reduction in fetal weights and fetal brain weights, or (3) a reduction in the level of VIP mRNA in embryos. In the context of neuronal death, "an amount sufficient" or "an effective amount" is that amount of a given ADNF polypeptide that reduces neuronal cell death in the assays of, e.g., Hill et al., *Brain Res.* 603, 222–233 (1993); Venner & Gupta, *Nucleic Acid Res.* 18, 5309 (1990); Peralta et al., *Nucleic Acid Res.* 18, 7162 (1990); Brenneman et al., *Nature* 335, 636 (1988); or Brenneman et al., *Dev. Brain Res.* 51:63 (1990); Forsythe & Westbrook *Physiol. Lond.* 396:515 (1988). The dosing range can vary depending on the ADNF polypeptide used, the route of administration and the potency of the particular ADNF polypeptide, but can readily be determined using the foregoing assays.

The term "biologically active" refers to a peptide sequence that will interact with naturally occurring biological molecules to either activate or inhibit the function of those molecules in vitro or in vivo. The term "biologically active" is most commonly used herein to refer to ADNF polypeptides or subsequences thereof that exhibit neuroprotective/neurotrophic action on neurons originating in the central nervous system either in vitro or in vivo. The neuroprotective/neurotrophic action of ADNF polypeptides can be tested using, e.g., cerebral cortical cultures treated with a neurotoxin (see, Gozes et al., *Proc. Nat'l. Acad. Sci. USA* 93:427–432 (1996)).

The terms "isolated," "purified," or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated ADNF nucleic acid is separated from open reading frames that flank the ADNF gene and encode proteins other than ADNF. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

The terms "polypeptide," "peptide," and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers.

The term "amino acid" refers to naturally occurring amino acids, amino acid analogs, and amino acid mimetics that function in a manner similar to the naturally occurring and analog amino acids. Naturally occurring amino acids are those encoded by the genetic code, as well as those amino acids that are later modified, e.g., hydroxyproline, γ-carboxyglutamate, and O-phosphoserine. Amino acid analogs refers to synthetic amino acids that have the same basic chemical structure as a naturally occurring amino acid, i.e., an a carbon that is bound to a hydrogen, a carboxyl group, an amino group, and an R group (e.g., homoserine, norleucine, methionine sulfoxide, methionine methyl sulfonium). Such analogs have modified R groups (e.g., norleucine) or modified peptide backbones, but retain the same basic chemical structure as a naturally occurring amino acid. Both naturally occurring and analog amino acids can be made synthetically. Amino acid mimetics refer to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W).
(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides (i.e., 70% identity) that are the same, when compared and aligned for maximum correspondence over a comparison window, as measured using one of the following sequence comparison algorithms or by manual alignment and visual inspection. Such sequences are then said to be "substantially identical." This definition also refers to the complement of a test sequence. Preferably, the percent identity exists over a region of the sequence that is at least about 25 amino acids in length, more preferably over a region that is 50 or 100 amino acids in length.

For sequence comparison, one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nucleic Acids Res.* 12:387–395 (1984)).

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et at, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, *Proc. Nati. Acad. Sci.* USA 89:10915 (1989)) alignments (B) of 50, expectation (E) of 10, $M=5$, $N=-4$, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with a wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers or a pool of degenerate primers that encode a conserved amino acid sequence, can then be used as a probe under stringent hybridization conditions to isolate the test sequence from a cDNA or genomic library, or to identify the test sequence in, e.g., a northern or Southern blot. Alternatively, another indication that the sequences are substantially identical is if the same set of PCR primers can be used to amplify both sequences.

DETAILED DESCRIPTION OF THE INVENTION AND PREFERRED EMBODIMENTS

I. Introduction

It has now been discovered that polypeptides derived from the neurotrophic proteins ADNF I and ADNF III are effective for reducing a condition associated with fetal alcohol syndrome in a subject who is exposed to alcohol in utero. In a preferred embodiment, it has been found that treatment with combination of an ADNF I polypeptide and an ADNF III polypeptide has a remarkable synergistic effect in reducing or preventing a condition associated with fetal alcohol syndrome. In addition, it has now been discovered that combination of an ADNF I polypeptide and an ADNF III polypeptide is effective for reducing neuronal cell death.

As such, the present invention provides, inter alia, a method for reducing a condition associated with fetal alcohol syndrome in a subject who is exposed to alcohol in utero with an ADNF polypeptides. In particular, the present invention provides a method for reducing a condition associated with fetal alcohol syndrome in a subject who is exposed to alcohol in utero with a combination of ADNF I and ADNF III polypeptides. The present invention also provides a method for reducing neuronal cell death by contacting neuronal cells with a combination of ADNF I and ADNF III polypeptides in an amount sufficient to reduce neuronal cell death. Still further, the present invention provides a pharmaceutical composition comprising a pharmaceutically acceptable excipient and a combination of ADNF I and ADNF III polypeptides.

In addition, the ADNF polypeptides of the present invention, in particular a combination of ADNF I and ADNF III polypeptides, can be used to treat numerous forms of neurodegeneration (see Lipton & Rosenberg, New Eng. J. Med. 330:613–622 (1994), the teaching of which are incorporated herein by reference for all purposes). Such neurodegeneration includes, but is not limited to, the following: Huntington's disease; AIDS dementia complex; neuropathic pain syndromes; olivopontocerebellar atrophy; parkinsonism and Parkinson's disease; amyotrophic lateral sclerosis; mitochondrial abnormalities and other inherited or acquired biochemical disorders; MELAS syndrome; MERRF; Leber's disease; Wernicke's encephalopathy; Rett syndrome; homocysteinuria; hyperprolinemia; nonketotic hyperglycinemia; hydroxybutyric aminoaciduria; sulfite oxide deficiency; combined systems disease; lead encephalopathy; Alzheimer's disease; hepatic encephalopathy; Tourette's syndrome; Down's syndrome; developmental retardation and learning impairments; closed head trauma; dopamine toxicity; drug addiction, tolerance, and dependency. Those of skill in the art will appreciate that the above list is merely illustrative and that the ADNF polypeptides of the present invention can be used to treat other neurological disorders.

II. Methods for Reducing Fetal Alcohol Syndrome

In one aspect, the present invention provides a method for reducing a condition associated with fetal alcohol syndrome in a subject who is exposed to alcohol in utero, the method comprising administering to the subject an ADNF polypeptide in an amount sufficient to reduce the condition associated with fetal alcohol syndrome. Treatment of a well-characterized model for FAS (e.g., C57B/6J mouse strain) with an ADNF polypeptide reduces or prevents alcohol induced fetus death, body and brain weight reduction, and VIP mRNA reduction. Similarly, the human embryo, fetus, or subject can be protected from alcohol induced effects by administering an ADNF polypeptide directly to the embryo, fetus, or subject, or by administering the ADNF polypeptide indirectly to the fetus by administering it to the mother.

In one embodiment, the ADNF I polypeptide comprises an amino acid sequence of $(R^1)_x$-Ser-Ala-Leu-Leu-Arg-Ser-Ile-Pro-Ala-$(R^2)_y$ (SEQ ID NO:3), and the ADNF III polypeptide comprises an amino acid sequence of $(R^3)_w$-Asn-Ala-Pro-Val-Ser-Ile-Pro-Gln-$(R^4)_z$ (SEQ ID NO:4). In another embodiment, x and y are both zero for the above formula for the ADNF I polypeptide (SEQ ID NO:1), and w and z are both zero for the above formula for the ADNF III polypeptide (SEQ ID NO:2).

In the above formula, each of $R^1$, $R^2$, $R^3$, and $R^4$, if present, is an amino acid sequence comprising from 1 to about 40 amino acids wherein each amino acid is independently selected. The term "independently selected" is used herein to indicate that the amino acids making up, for example, the amino acid sequence $R^1$ may be identical or different (e.g., all of the amino acids in the amino acid sequence may be threonine, etc.). Moreover, as previously explained, the amino acids making up the amino acid sequence $R^1$ may be either naturally occurring amino acids, or known analogues of natural amino acids that functions in a manner similar to the naturally occurring amino acids (i.e., amino acid mimetics). This discussion pertaining to $R^1$ is fully applicable to $R^2$, $R^3$, and $R^4$.

Within the above formula for the ADNF I polypeptide, x and y are independently selected and are equal to zero or one. The term independently selected is used herein to indicate that x and y may be identical or different. For example, x and y may both be zero or, alternatively, x and y may both be one. In addition, x may be zero and y may be one or, alternatively, x may be one and y may be zero. Moreover, if x and y are both one, the amino acid sequences $R^1$ and $R^2$ may be the same or different. As such, the amino acid sequences $R^1$ and $R^2$ are independently selected. If $R^1$ and $R^2$ are the same, they are identical in terms of both chain length and amino acid composition. For example, both $R^1$ and $R^2$ may be Val-Leu-Gly-Gly-Gly (SEQ ID NO:5) SEQ ID NO:14. If $R^1$ and $R^2$ are different, they can differ from one another in terms of chain length and/or amino acid composition and/or order of amino acids in the amino acids sequences. For example, $R^1$ may be Val-Leu-Gly-Gly-Gly (SEQ ID NO:5), whereas $R^2$ may be Val-Leu-Gly-Gly (SEQ ID NO:9) (SEQ ID NO:9). Alternatively, $R^1$ may be Val-Leu-Gly-Gly-Gly (SEQ ID NO:5), whereas $R^2$ may be Val-Leu-Gly-Gly-Val (SEQ ID NO:10); SEQ ID NO:16. Alternatively, $R^1$ may be Val-Leu-Gly-Gly-Gly (SEQ ID NO:5), whereas $R^2$ may be Gly-Val-Leu-Gly-Gly (SEQ ID NO: 11); SEQ ID NO:17.

Similarly, w and z are independently selected and are equal to zero or one within the above formula for the ADNF III polypeptide. The term independently selected is used herein to indicate that w and z may be identical or different. For example, w and z may both be zero or, alternatively, w and z may both be one. In addition, w may be zero and z may be one or, alternatively, w may be one and z may be zero. Moreover, if w and z are both one, the amino acid sequences $R^3$ and $R^4$ may be the same or different. As such, the amino acid sequences $R^3$ and $R^4$ are independently selected. If $R^3$ and $R^4$ are the same, they are identical in terms of both chain length and amino acid composition. For example, both $R^3$ and $R^4$ may be Leu-Gly-Leu-Gly-Gly (SEQ ID NO:7); SEQ ID NO:18. If $R^3$ and $R^4$ are different, they can differ from one another in terms of chain length and/or amino acid composition and/or order of amino acids in the amino acids sequences. For example, $R^3$ may be Leu-Gly-Leu-Gly-Gly (SEQ ID NO:7), whereas $R^4$ may be Leu-Gly-Leu-Gly (SEQ ID NO: 12); SEQ ID NO:19. Alternatively, $R^3$ may be Leu-Gly-Leu-Gly-Gly (SEQ ID NO:7), whereas $R^4$ may be Leu-Gly-Leu-Gly-Leu (SEQ ID NO: 13); SEQ ID NO:20.

Within the scope, certain ADNF I and ADNF III polypeptides are preferred, namely those in which x, y, w, and z are all zero (i.e., SALLRSIPA (SEQ ID NO:1) and NAPVSIPQ (SEQ ID NO:2), respectively). Equally preferred are ADNF I polypeptides in which x is one; $R^1$ is Val-Leu-Gly-Gly-Gly (SEQ ID NO:5); and y is zero; SEQ ID NO:21. Also equally preferred are ADNF I polypeptides in which x is one; $R^1$ is Val-Glu-Glu-Gly-Ile-Val-Leu-Gly-Gly-Gly (SEQ ID NO:6); and y is zero; SEQ ID NO:22. Also equally preferred are ADNF III polypeptides in which w is one; $R^3$ is Gly-Gly; and z is zero; SEQ ID NO:23. Also equally preferred are ADNF III polypeptides in which w is one; $R^3$ is Leu-Gly-Gly; z is one; and $R^4$ is Gln-Ser; SEQ ID NO:24. Also equally preferred are ADNF III polypeptides in which w is one; $R^3$ is Leu-Gly-Leu-Gly-Gly- (SEQ ID NO:7); z is one; and $R^4$ is Gln-Ser; SEQ ID NO:25. Also equally preferred are ADNF III polypeptides in which w is one; $R^3$ is Ser-Val-Arg-Leu-Gly-Leu-Gly-Gly (SEQ ID NO:8); z is one; and $R^4$ is Gln-Ser; SEQ ID NO:26. Additional amino acids can be added to both the N-terminus and the C-terminus of these active sites (SALLRSIPA (SEQ ID NO:1) or NAPVSIPQ (SEQ ID NO:2)) without loss of biological activity as evidenced by the fact that the intact ADNF I or ADNF III growth factors exhibit extraordinary biological activity. See, U.S. Ser. No. 08/324,297, filed Oct. 17, 1994 (also published as WO96/11948) for the description of ADNF I polypeptides; and U.S. Ser. No. 60/037,404 filed Feb. 27, 1997 and U.S. Ser. No. 60/059,621 filed, Sep. 23, 1997 (also published as WO98/35042) for the description of ADNF III polypeptides, all of which are incorporated herein by reference.

Other ADNF polypeptides (including their alleles, polymorphic variants, species homologs and subsequences thereof) that reduce a condition associated with fetal alcohol syndrome can be screened using a well-characterized animal model for FAS. For example, the C57B 1/6J mouse strain can be used. Previous work with this strain has defined the effects of dosage and embryonic timing on maternal serum alcohol levels and embryonic effects (Webster et al., *Neurobehav. Tox.*, 2:227–34 (1980), incorporated herein by reference). Intra-peritoneal treatment allows for defined and reproducible dosages. Acute (single) dosages of alcohol can reproduce the phenotype of FAS (Webster et al., (1980), supra). Since treatment on E8 results in the highest rate of fetal anomalies and demises, and vasoactive intestinal peptide's growth regulating effects on the embryo are limited to the early post-implantation period of embryogenesis, E8 can be chosen as a test for screening neuroprotective ADNF polypeptides. The mice can be injected with 25% ethyl alcohol in saline (v/v) or vehicle alone at, e.g., 0.030 ml/g maternal body weight at, e.g., 9:00 a.m. on E8 (embryonic gestation day 8). ADNF polypeptides can be screened by pretreating the mice 30 minutes prior to alcohol administration. In one embodiment, the dose for nasal administration for an ADNF polypeptide is about 1 µg–50 µg, preferably about 1 µg–10 µg/mouse. This dose is based on the average body weight of mice, and an appropriate dose for human can be extrapolated based on the average body weight of human.

Various parameters can be measured to determine if an ADNF polypeptide or a combination of ADNF polypeptides reduce a condition associated with fetal alcohol syndrome. For example, a number of fetal demises (i.e., death) can be compared between the control (e.g., untreated with ADNF polypeptides) and a group pretreated with ADNF polypeptides. Alternatively, the fetal weight and fetal brain weight in the surviving E18 fetuses can be compared. Still further, the level of VIP mRNA can be compared between the control and a group treated with ADNF polypeptides.

III. Methods for Reducing Neuronal Cell Death

In another aspect, the present invention provides a method for reducing neuronal cell death, the method comprising contacting neuronal cells with a combination of an ADNF I polypeptide and an ADNF III polypeptide in an amount sufficient to reduce neuronal cell death.

In one embodiment, the ADNF I and ADNF III polypeptides are full length polypeptides. In another embodiment, the ADNF I polypeptide comprises an amino acid sequence of $(R^1)_x$-Ser-Ala-Leu-Leu-Arg-Ser-Ile-Pro-Ala-$(R^2)_y$ (SEQ ID NO:3); and the ADNF III polypeptide comprises an amino acid sequence of $(R^3)_w$-Asn-Ala-Pro-Val-Ser-Ile-Pro-Gln-$(R^4)_z$ (SEQ ID NO:4). In another embodiment, x and y are both zero for the above formula for the ADNF I polypeptide, and w and z are both zero for the above formula for the ADNF III polypeptide.

The previous discussion pertaining to $R^1$, $R^2$, $R^3$, $R^4$, x, y, and w and z, and various ADNF polypeptide embodiments is fully applicable to the ADNF polypeptides used in this method of present invention and, thus, will not be repeated with respect to this particular method.

A combination of ADNF I and ADNF III polypeptides of the present invention can be used in the treatment of neurological deficiencies and for the prevention of neuronal cell death. For example, a combination of ADNF I and ADNF III polypeptides can be used to prevent the death of neuronal cells including, but not limited to, spinal cord neurons, hippocampal neurons, cerebral cortical neurons and cholinergic neurons. More particularly, a combination of ADNF I and ADNF III polypeptides of the present invention can be used in the prevention of cell death associated with (1) gp120, the envelope protein from HIV; (2) N-methyl-D-aspartic acid (excito-toxicity); (3) tetrodotoxin (blockage of electrical activity); and (4) β-amyloid peptide, a substance related to neuronal degeneration in Alzheimer's disease. Similarly, it will be readily apparent to those of skill in the art that a combination of ADNF I and ADNF III polypeptides of the present invention can be used in a similar manner to prevent neuronal cell death associated with a number of other neurological diseases and deficiencies. Pathologies that would benefit from therapeutic and diagnostic applications of this invention include conditions (diseases and insults) leading to neuronal cell death and/or sub-lethal neuronal pathology including, for example, the following:

diseases of central motor systems including degenerative conditions affecting the basal ganglia (Huntington's disease, Wilson's disease, striatonigral degeneration, corticobasal ganglionic degeneration), Tourette's syndrome, Parkinson's disease, progressive supranuclear palsy, progressive bulbar palsy, familial spastic paraplegia, spinomuscular atrophy, ALS and variants thereof, dentatorubral atrophy, olivopontocerebellar atrophy, paraneoplastic cerebellar degeneration, and dopamine toxicity;

diseases affecting sensory neurons such as Friedreich's ataxia, diabetes, peripheral neuropathy, retinal neuronal degeneration;

diseases of limbic and cortical systems such as cerebral amyloidosis, Pick's atrophy, Retts syndrome;

neurodegenerative pathologies involving multiple neuronal systems and/or brainstem including Alzheimer's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of CNS degeneration;

pathologies associated with developmental retardation and learning impairments, and Down's syndrome, and oxidative stress induced neuronal death;

pathologies arising with aging and chronic alcohol or drug abuse including, for example, with alcoholism the degeneration of neurons in locus coeruleus, cerebellum, cholinergic basal forebrain; with aging degeneration of cerebellar neurons and cortical neurons leading to cognitive and motor impairments; and with chronic amphetamine abuse degeneration of basal ganglia neurons leading to motor impairments;

pathological changes resulting from focal trauma such as stroke, focal ischemia, vascular insufficiency, hypoxic-ischemic encephalopathy, hyperglycemia, hypoglycemia, closed head trauma, or direct trauma;

pathologies arising as a negative side-effect of therapeutic drugs and treatments (e.g., degeneration of cingulate and entorhinal cortex neurons in response to anticonvulsant doses of antagonists of the NMDA class of glutamate receptor).

Other combinations of ADNF I and ADNF III polypeptides (including their alleles, polymorphic variants, species homologs and subsequences thereof) that reduce neuronal cell death can be screened using the various methods described in U.S. Ser. No. 60/037,404, filed Feb. 27, 1997 (published as WO98/35042), and U.S. Ser. No. 09/187,330 filed Nov. 6, 1998, both of which are incorporated herein by reference. For example, it will be readily apparent to those skilled in the art that using the teachings set forth above with respect to the design and synthesis of ADNF polypeptides and the assays described herein, one of ordinary skill in the art can identify other combinations of ADNF polypeptides which can reduce neuronal cell death. For example, Brenneman et al., *Nature* 335, 636 (1988), and Dibbern et al., *J. Clin. Invest.* 99:2837–2841 (1997), incorporated herein by reference, teach assays that can be used to screen combinations of ADNF I and ADNF III polypeptides that are capable of reducing neuronal cell death associated with envelope protein (gp120) from HIV. Also, Brenneman et al., *Dev. Brain Res.* 51:63 (1990), and Brenneman & Gozes, *J. Clin. Invest.* 97:2299–2307 (1996), incorporated herein by reference, teach assays that can be used to screen combinations of ADNF I and ANDF III polypeptides which are capable of reducing neuronal cell death associated with excito-toxicity induced by stimulation by N-methyl-D-asparate. Furthermore, Venner & Gupta, *Nucleic Acid Res.* 18, 5309 (1990) and Peralta et al., *Nucleic Acid Res.* 18, 7162 (1990), incorporated herein by reference, teach assays that can be used to screen combinations of ADNF I and ADNF III polypeptides which are capable of reducing TTX-induced neuronal cell death. Other assays described in, e.g., WO98/35042 can be used to identify ADNF polypeptides which can be used to reduce neuronal cell death associated with other clinical conditions.

Moreover, combinations of ADNF I and ADNF III polypeptides that reduce neuronal cell death can be screened in vivo. For example, the ability of combinations of ADNF I and ADNF III polypeptides that can protect against learning and memory deficiencies associated with cholinergic blockade can be tested. For example, cholinergic blockade can be obtained in rats by administration of the cholinotoxin AF64A, and a combination of ADNF I and ADNF III polypeptides can be administered intranasally and the water maze experiments can be performed (Gozes et al., *Proc. Natl. Acad. Sci. USA* 93:427–432 (1996), the teachings of which are incorporated herein by reference). Animals treated with an efficacious combination of ADNF I and ADNF III polypeptides would show improvement in their learning and memory capacities compared to the control.

Furthermore, the ability of combinations of ADNF I and ADNF III polypeptides that can protect or reduce neuronal cell death associated with Alzheimer's disease can be screened in vivo. For these experiments, apolipoprotein E (ApoE)-deficient homozygous mice can be used (Plump et al., *Cell* 71:343–353 (1992); Gordon et al., *Neuroscience Letters* 199:1–4 (1995); Gozes et al., *J. Neurobiol.* 33:329–342 (1997)), the teachings of which are incorporated herein by reference.

In the above assays, various permutations of ADNF I and ADNF III polypeptides can be combined to determine a combination which provides the best result in terms of reduction of neuronal cell death. In each combination, the proportion of ADNF I and ADNF III polypeptides can be equal or different. The proportion of ADNF I and ADNF III polypeptides can be adjusted until combinations which provide the most efficacious formulations in reducing neuronal cell death are found.

IV. Pharmaceutical Compositions

In still yet another aspect, the present invention provides pharmaceutical compositions comprising one of the previously described combinations of ADNF I and ADNF III polypeptides in an amount sufficient to exhibit neuroprotective/neurotrophic activity, and a pharmaceutically acceptable diluent, carrier or excipient. In one embodiment, the ADNF I and ADNF III polypeptides are full length polypeptides. In another embodiment, the ADNF I polypeptide comprises an amino acid sequence of $(R^1)_x$-Ser-Ala-Leu-Leu-Arg-Ser-Ile-Pro-Ala-$(R^2)_y$ (SEQ ID NO:3); and the ADNF III polypeptide comprises an amino acid sequence of $(R^3)_w$-Asn-Ala-Pro-Val-Ser-Ile-Pro-Gln-$(R^4)_z$ (SEQ ID NO:4). In another embodiment, x, y, w, and z are all zero for the above formula for the ADNF I polypeptide (SEQ ID NO:1) and for the ADNF III polypeptide (SEQ ID NO:2).

The previous discussion pertaining to $R^1$, $R^2$, $R^3$, $R^4$, x, y, w, and z, and various ADNF polypeptide embodiments is fully applicable to the ADNF I and ADNF III polypeptides used in this method of the present invention and, thus, will not be repeated with respect to this particular method.

The pharmaceutical compositions of the present invention are suitable for use in a variety of drug delivery systems. Suitable formulations for use in the present invention are found in *Remington's Pharmaceutical Sciences* (17th ed. 1985)), which is incorporated herein by reference. In addition, for a brief review of methods for drug delivery, see Langer, *Science* 249:1527–1533 (1990), which is incorporated herein by reference.

Due to their ability to increase growth and survival of neurons, a combination of ADNF I and ADNF III polypeptides has extensive uses in the treatment of neurological deficiencies that result, for example, from neuronal development, aging, neurodegenerative diseases or spinal cord injury. As such, the present invention provides for therapeutic compositions or medicaments comprising a combination of one or more of the ADNF I and ADNF III polypeptides described herein above in combination with a pharmaceutically acceptable excipient, wherein the amount of a combination the ADNF I and ADNF III polypeptide is sufficient to provide a desirable therapeutic effect.

Small polypeptides including SALLRSIPA (SEQ ID NO:1) and NAPVSIPQ (SEQ ID NO:2)cross the blood brain barrier. For longer polypeptides that do not the cross blood brain barrier, methods of administering proteins to the brain are well known. For example, proteins, polypeptides, other compounds and cells can be delivered to the mammalian brain via intracerebroventricular (ICV) injection or via a cannula (see, e.g., Motta & Martini, *Proc. Soc. Exp. Biol. Med.* 168:62–64 (1981); Peterson et al., *Biochem. Pharamacol.* 31:2807–2810 (1982); Rzepczynski et al., *Metab. Brain Dis.* 3:211–216 (1988); Leibowitz et al., *Brain Res. Bull.* 21:905–912 (1988); Sramka et al., *Stereotact. Funct. Neurosurg.* 58:79–83 (1992); Peng et al., *Brain Res.* 632:57–67 (1993); Chem et al., *Exp. Neurol.* 125:72–81 (1994); Nikkhah et al., *Neuroscience* 63:57–72 (1994); Anderson et al., *J. Comp. Neurol.* 357:296–317 (1995); and Brecknell & Fawcett, *Exp. Neurol.* 138:338–344 (1996)). In particular, cannulas can be used to administer neurotrophic factors to mammals (see, e.g., Motta & Martini, *Proc. Soc. Exp. Biol. Med.* 168:62–64 (1981) (neurotensin); Peng et al., *Brain Res.* 632:57–67 (1993) (NGF); Anderson et al., *J. Comp. Neurol.* 357:296–317 (1995) (BDNF, NGF, neurotrophin-3).

Furthermore, the ADNF I and ADNF III polypeptides of the present invention are embodied in pharmaceutical compositions intended for parenteral, topical, oral or local administration. Preferably, the pharmaceutical compositions are administered parenterally, e.g., intravenously, subcutaneously, intradermally, or intramuscularly, or intranasally. Thus, the invention provides compositions for parenteral administration that comprise a solution of a combination of ADNF I and ADNF III polypeptides, as described above, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For solid compositions, conventional nontoxic solid carriers may be used that include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, a combination of ADNF I and ADNF III polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In therapeutic applications, a combination of ADNF I and ADNF III polypeptides of the invention are administered to a patient in an amount sufficient to prevent neuronal cell death. An amount adequate to accomplish this is defined as "therapeutically effective dose." Amounts effective for this use will depend on, for example, the particular ADNF I or ADNF III polypeptide employed, the type of neuronal cell death or damage to be prevented, the manner of administration, the weight and general state of health of the patient, and the judgment of the prescribing physician. For example, for the prevention of neuronal cell death, an amount of ADNF I or ADNF III polypeptides falling within the range of a 1 µg to 50 µg, preferably 1 µg to 10 µg dose given intranasally once a day per mouse (e.g., in the evening) would be a therapeutically effective amount. This dose is based on the average body weight of a mouse. Therefore, an appropriate dose can be extrapolated for a human body.

Alternatively, nucleic acids encoding ADNF can also be used to provide a therapeutic dose of ADNF polypeptides. These nucleic acids can be inserted into any of a number of well-known vectors for the transfection of target cells and organisms. For example, nucleic acids are delivered as DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808–813 (1992); Nabel & Felgner, *TIBTECH* 11:211–217 (1993); Mitani & Caskey, *TIBTECH* 11:162–166 (1993); Dillon, *TIBTECH* 11:167–175 (1993); Miller, *Nature* 357:455–460 (1992); Van Brunt, *Biotechnology* 6(10):1149–1154 (1988); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* Doerfler and Böhm (eds) (1995); and Yu et al., *Gene Therapy* 1:13–26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. No. 5,049,386, U.S. Pat. No. 4,946,787; and U.S. Pat. No. 4,897,355) and lipofection reagents are sold commercially (e.g., TRANSFECTAM™ (dioctadecylamidoglycyl spermine) and LIPOFECTIN™ (cationic liposomes). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

V. Methods for Production of ADNF Polypeptides

A. Recombinant Methods for Production of ADNF Polypeptides

1. Cloning and Isolation of ADNF Nucleic Acids

Several specific nucleic acids encoding ADNF polypeptides are described herein. See, also, e.g., Brenneman & Gozes, *J. Clin. Invest.* 97:2299–2307 (1996), Brenneman, *J. Pharm. Exp. Ther.* 285:619–627 (1998), and Bassan et al. *J. Neurochem* 72:1283–1293 (1999), the teachings of which are hereby incorporated in their entirety by reference. These nucleic acids can be made using standard recombinant or synthetic techniques. Given the nucleic acids of the present invention, one of skill can construct a variety of clones containing functionally equivalent nucleic acids, such as nucleic acids that encode the same ADNF polypeptides. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Sambrook et al., *Molecular Cloning—A Laboratory Manual* (2nd ed. 1989) and *Current Protocols in Molecular Biology* (Ausubel et al., eds., 1994).

In addition, product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

The nucleic acid compositions of this invention, whether RNA, cDNA, genomic DNA or a hybrid of the various combinations, are isolated from biological sources, such as astrocyte, neuroblastoma cells, or fibroblasts, or synthesized in vitro. The nucleic acids of the invention are present in transformed or transfected cells, in transformed or transfected cell lysates, or in a partially purified or substantially pure form.

In vitro amplification techniques suitable for amplifying sequences for use as molecular probes or generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification and other RNA polymerase mediated techniques (e.g., NASBA), are found in Berger, Sambrook et al. and Ausubel et al., all supra, as well as in U.S. Pat. No. 4,683,202; *PCR Protocols A Guide to Methods and Applications* (Innis et al., eds., 1990); Arnheim & Levinson (Oct. 1, 1990) *C&EN* 36–47; *The Journal Of NIH Research* 3:81–94 (1991); Kwoh et al., *Proc. Natl. Acad. Sci. USA* 86:1173 (1989); Guatelli et al., *Proc. Natl. Acad. Sci. USA* 87:1874 (1990); Lomell et al., *J. Clin. Chem* 35:1826 (1989); Landegren et al., *Science* 241:1077–1080 (1988); Van Brunt, *Biotechnology* 8:291–294 (1990); Wu & Wallace, *Gene* 4:560 (1989); Barringer et al., *Gene* 89:117 (1990); and Sooknanan & Malek, *Biotechnology* 13:563–564 (1995). Improved methods of cloning in vitro amplified nucleic acids are described in U.S. Pat. No. 5,426,039. Improved methods of amplifying large nucleic acids are summarized in Cheng et al., *Nature* 369:684–685 (1994) and the references therein. One of skill will appreciate that essentially any RNA can be converted into a double stranded DNA suitable for restriction digestion, PCR expansion and sequencing using reverse transcriptase and a polymerase.

Oligonucleotides for use as probes, for example, with in vitro ADNF nucleic acid amplification methods, or for use as nucleic acid probes to detect ADNF nucleic acids, are typically synthesized chemically according to the solid phase phosphoramidite triester method described by Beaucage & Caruthers, *Tetrahedron Letts.*, 22(20):1859–1862 (1981), e.g., using an automated synthesizer, e.g., as described in Needham-VanDevanter et al., *Nucleic Acids Res.* 12:6159–6168 (1984). Oligonucleotides can also be custom made and ordered from a variety of commercial sources known to those of skill in the art. Purification of oligonucleotides, where necessary, is typically performed by either native acrylamide gel electrophoresis, or by anion-exchange HPLC as described in Pearson & Regnier, *J. Chrom.* 255:137–149 (1983). The sequence of the synthetic oligonucleotides can be verified using the chemical degradation method of Maxam & Gilbert, in *Methods in Enzymology* 65:499–560 (Grossman & Moldave, eds., 1980).

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see, Giliman & Smith, *Gene* 8:81–97 (1979); Roberts et al., *Nature* 328:731–734 (1987); and Sambrook et al., *Molecular Cloning—A Laboratory Manual* (2nd ed. 1989)).

2. Recombinant Expression of ADNF Polypeptides

In one embodiment, the polypeptides, or subsequences thereof, are synthesized using recombinant nucleic acid methodology. Generally, this involves creating a nucleic acid sequence that encodes the protein, placing the nucleic acid in an expression cassette under the control of a particular promoter, expressing the protein in a host cell, isolating the expressed protein and, if required, renaturing the protein.

Once a nucleic acid encoding an ADNF polypeptide of the invention is isolated and cloned, the nucleic acid is optionally expressed in recombinantly engineered cells known to those of skill in the art. Examples of such cells include, but are not limited to, bacteria, yeast, plant, filamentous fungi, insect (especially employing baculoviral vectors) and mammalian cells. The recombinant nucleic acids are operably linked to appropriate control sequences for expression in the selected host. For *E. coli*, example control sequences include the T7, trp, or lambda promoters, a ribosome binding site and, preferably, a transcription termination signal. For eukaryotic cells, the control sequences typically include a promoter and, preferably, an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods. Such methods include, for example, the calcium chloride transformation method for *E. coli* and the calcium phosphate treatment or electroporation methods for mammalian cells. Cells transformed by the plasmids can be selected by resistance to antibiotics conferred by genes contained on the plasmids, such as the amp, gpt, neo, and hyg genes.

Once expressed, the recombinant ADNF polypeptides or naturally occurring can be purified according to standard procedures of the art, including ammonium sulfate precipitation, affinity columns, column chromatography, gel electrophoresis and the like (see, e.g., Scopes, *Polypeptide Purification* (1982); Deutscher, *Methods in Enzymology Vol. 182: Guide to Polypeptide Purification* (1990)). Once purified, partially or to homogeneity as desired, the ADNF polypeptides may then be used, e.g., to prevent neuronal cell death or to treat a condition associated with fetal alcohol syndrome. See, also, e.g., Brenneman & Gozes, *J. Clin. Invest.* 97:2299–2307 (1996), Brenneman et al., *J. Pharm. Exp. Ther.* 285:619–627 (1998), and Bassan et al. *J. Neurochem* 72:1283–1293 (1999), the teachings of which are hereby incorporated in their entirety by reference.

B. Synthesis of ADNF Polypeptides

In addition to the foregoing recombinant techniques, the ADNF polypeptides of the invention are optionally synthetically prepared via a wide variety of well-known techniques. Polypeptides of relatively short size are typically synthesized in solution or on a solid support in accordance with conventional techniques (see, e.g., Merrifield, *Am. Chem. Soc.* 85:2149–2154 (1963)). Various automatic synthesizers and sequencers are commercially available and can be used in accordance with known protocols (see, e.g., Stewart & Young, *Solid Phase Peptide Synthesis* (2nd ed. 1984)). Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany & Merrifield, *Solid-Phase Peptide Synthesis*; pp. 3–284 in *The Peptides: Analysis, Synthesis, Biology. Vol. 2: Special Methods in Peptide Synthesis, Part A.*; Merrifield et al., *J. Am. Chem. Soc.* 85:2149–2156 (1963); and Stewart et al., *Solid Phase Peptide Synthesis* (2nd ed. 1984).

After chemical synthesis, biological expression or purification, the polypeptide(s) may possess a conformation substantially different than the native conformations of the constituent polypeptides. In this case, it is helpful to denature and reduce the polypeptide and then to cause the polypeptide to re-fold into the preferred conformation. Methods of reducing and denaturing polypeptides and inducing re-folding are well known to those of skill in the art (see Debinski et al., *J. Biol. Chem.* 268:14065–14070 (1993); Kreitman & Pastan, *Bioconjug. Chem.* 4:581–585 (1993); and Buchner et al., *Anal. Biochem.* 205:263–270 (1992)). Debinski et al., for example, describe the denaturation and reduction of inclusion body polypeptides in guanidine-DTE. The polypeptide is then refolded in a redox buffer containing oxidized glutathione and L-arginine.

One of skill will recognize that modifications can be made to the polypeptides without diminishing their biological activity. Some modifications may be made to facilitate the cloning, expression, or incorporation of the targeting molecule into a fusion polypeptide. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

C. Conservative Modifications of the ADNF Nucleic Acids and Polypeptides

One of skill will appreciate that many conservative variations of the ADNF nucleic acid and polypeptide sequences provided herein yield functionally identical products. For example, due to the degeneracy of the genetic code, "silent substitutions" (i.e., substitutions of a nucleic acid sequence that do not result in an alteration in an encoded polypeptide) are an implied feature of every nucleic acid sequence that encodes an amino acid. Similarly, "conservative amino acid substitutions," in one or a few amino acids in an amino acid sequence are substituted with different amino acids with highly similar properties (see the definitions section, supra), are also readily identified as being highly similar to a disclosed amino acid sequence, or to a disclosed nucleic acid sequence that encodes an amino acid. Such conservatively substituted variations of each explicitly listed nucleic acid and amino acid sequences are a feature of the present invention.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see Giliman & Smith, *Gene* 8:81–97 (1979); Roberts et al., *Nature* 328:731–734 (1987)). For example, alanine scanning can be used to determine conservatively modified variants for SALLRSIPA (SEQ ID NO:1) or NAPVSIPQ (SEQ ID NO:2) (i.e., by substituting each amino acid one by one with an alanine or other small neutral amino acid and assay for activity as described herein).

Polypeptide sequences can also be altered by changing the corresponding nucleic acid sequence and expressing the polypeptide. Polypeptide sequences are also optionally generated synthetically using commercially available peptide synthesizers to produce any desired polypeptide (see, Merrifield, supra, and Stewart & Young, supra).

More particularly, it will be readily apparent to those of ordinary skill in the art that the ADNF polypeptides of the present invention can readily be screened for neuroprotective/neurotrophic activity by employing the following CNS assay. Cerebral cortical cell cultures are prepared using the techniques described by Forsythe & Westbrook, *J. Physiol. Lond.* 396:515 (1988) with the following modifications. Cerebral cortex are used instead of hippocampus, and newborn rats are used instead of E16 mice. After nine days growth in vitro, the cultures are given a complete change of medium and treated with the ADNF polypeptide of interest (dissolved in phosphate buffered saline) for an additional five days. To terminate, the cells are fixed for immunocytochemistry and neurons identified with antibodies against NSE (i.e., neuron specific enolase, a neuronal specific marker). Cell counts are performed on 30 fields, with total area of about 15 mm$^2$. Neurons are counted without knowledge of treatment. Control counts not treated with any drugs should run for purposes of comparison. Furthermore, assays described by, e.g., Hill et al., *Brain Res.* 603, 222–233 (1993); Venner & Gupta., *Nucleic Acid Res.* 18, 5309 (1990); and Peralta et al., *Nucleic Acid Res.* 18, 7162 (1990) can be used.

Using these assays, one of ordinary skill in the art can readily prepare a large number of ADNF polypeptides in accordance with the teachings of the present invention and, in turn, screen them using the foregoing assay to find ADNF polypeptides, in addition to those set forth herein, which possess the neuroprotective/neurotrophic activity of the intact ADNF growth factor. For instance, using ADNF III-8 (i.e., Asn-Ala-Pro-Val-Ser-Ile-Pro-Gln; SEQ ID NO:2) as a starting point, one can systematically add, for example, Gly-, Gly-Gly-, Leu-Gly-Gly- to the N-terminus of ADNF III-8 and, in turn, screen each of these ADNF III polypeptides in the foregoing assay to determine whether they possess neuroprotective/neurotrophic activity. In doing so, it will be found that additional amino acids can be added to both the N-terminus and the C-terminus of the newly discovered active site, i.e., Asn-Ala-Pro-Val-Ser-Ile-Pro-Gln (SEQ ID NO:2), without loss of biological activity as evidenced by the fact that the intact ADNF III growth factor exhibits extraordinary biological activity. This discussion also applies to ADNF I polypeptides.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

I. Materials and Methods

A. Animals

C57-B16J female mice (Jackson Labs) were kept under a 12 h light, 12 h dark regimen with food and water available at all times. The mice received humane animal care in compliance with the "Guideline for Care and Use of Experimental Animals." Six week old females (21–24 grams) were mated with C57-B 16J males for 4 h. The presence of a vaginal plug was considered day 0 pregnancy.

B. Treatment Groups

A published well-delineated model for FAS was followed (Webster, W. S., et al., *Neurobehav Tox,* 2:227–34 (1980)). Animals were injected (intraperitoneal) on E8 with 255 ethyl alcohol in saline (v/v) or vehicle alone at 0.030 ml/g body weight. Pretreatment with VIP and ADNF peptides (NAPVSIPQ (SEQ ID NO:2), SALLRSIPA (SEQ ID NO:1), NAPVSIPQ (SEQ ID NO:2)+SALLRSIPA (SEQ ID NO:1)) were given 30 min prior to alcohol. Dosages of the neuropeptides were NAPVSIPQ (SEQ ID NO:2) (20 μg) and (40 μg), SALLRSIPA (SEQ ID NO:1) (20 μg), NAPVSIPQ (SEQ ID NO:2) (20 μg)+(20 μg); VIP (1 μg). A NAPVSIPQ (SEQ ID NO:2)+SALLRSIPA (SEQ ID NO:1) control group without alcohol was studied. NAPVSIPQ (SEQ ID NO:2) was diluted in 50 μl DMSO and diluted in filtered Dulbecco's phosphate buffered saline (DPBS). SAL was dissolved and diluted in filtered DPBS. VIP was dissolved in 20 μg glacial acetic acid and diluted in HPLC water and DPBS. Since the animals receiving alcohol were incapacitated for approximately 6 h following injection, food and water were withheld from all groups for the initial 6 hours after injection, to allow accurate assessment of fetal weights.

C. Evaluation of Fetal Weights/Litters

At E18 (embryonic gestation day 18), the number of live and demised fetuses was determined. Fetal weights and fetal brain weights were obtained for each fetus in the litter. The mean fetal weights were determined for each mother and this was used for statistical analysis.

D. mRNA and Protein Determination

At 6, 24 and 48 h after treatment (days 8, 9, and 10), conceptuses were explanted from the uterus within decidua (embryo, membranes, trophoblast, decidua, and fluid) and a piece of maternal cerebral cortex was removed from at least three different pregnant mice. Treatment groups were alcohol, control, and NAPVSIPQ (SEQ ID NO:2)+SALLRSIPA (SEQ ID NO:1)+alcohol with the NAPVSIPQ (SEQ ID NO:2)+SALLRSIPA (SEQ ID NO:1) given 30 min before alcohol. At least three samples were examined per group, in addition, embryo/decidual samples were pooled in groups of three. These samples were frozen on dry ice, and stored at −80° C. until analyzed for VIP levels. VIP levels were measured with enzyme linked immunosorbant assay (ELISA, Peninsula laboratories, Belmont, Calif.). The linear range of the ELISA for VIP is 0.04–2.0 ng/ml. Concentrations of VIP were calculated per mg protein. Detection limit of the ELISA was 0.5 ng/10 μg protein. Other samples were homogenized as previously described for mRNA quantitation (Spong et al., *Endocrinol* (In Press)). Quantitation of VIP mRNA was performed with mimic cDNA primers as previously described Spong et al., *Endocrinol* (In Press)). The crossover values, when the mimic cDNA crossed to product cDNA, from the treatment groups were compared to those from control groups.

E. VIP Binding

In vitro autoradiography with $^{125}$I-VIP was performed on 20 μm cryostat sections of pregnant uteri, 6, 24 and 48 h after treatment with control, alcohol or NAPVSIPQ (SEQ ID NO:2)+SALLRSIPA (SEQ ID NO:1)+alcohol as previously described (Dibbern et al., *J. Clin Invest* 99:2837–41 (1997)). The density of labeled VIP binding was analyzed by digitizing the film images using a Macintosh II-based image analysis system (IMAGE, Wane Rasband, Research Services Brance, NIMH). Density measurements were taken from 2 or more images, from each of 3 or more uteri. The specific binding was determined by subtracting the light transmittance from brain sections incubated with 10$^{-6}$M unlabeled VIP from total light transmittance.

F. Statistics

The mean litter pup and fetal brain weight was calculated, with the litter mean used for all statistical analysis. Percent demises were calculated by dividing the number of demises by the total number of fetuses (live plus demises). Statistical analysis included ANOVA for continuous variables, Mann-Whitney U for nonparametic data, Chi square for categorical variables or Fisher's exact test where appropriate [Statview 4.5 (Abacus Concepts, Inc., Berkeley, Calif.)] with $p<0.05$ considered significant. Results are presented as mean±standard error unless specified.

II. Results

The C57B 1/6J mouse strain provided a well-characterized model for FAS. Previous work with this strain has defined the effects of dosage and embryonic timing on maternal serum alcohol levels and embryonic effects (Webster et al., *Neurobehav Tox*, 2:227–34 (1980)), incorporated herein by reference. Intra-peritoneal treatment allowed for defined and reproducible dosages. Acute (single) dosages of alcohol were shown to reproduce the phenotype of FAS (Webster et al., (1980), supra). Since treatment on E8 resulted in the highest rate of fetal anomalies and demises, and vasoactive intestinal peptide's growth regulating effects on the embryo are limited to the early post-implantation period of embryogenesis, E8 was chosen as the test for the protective activity of the neuropeptides. The mice were injected with 25% ethyl alcohol in saline (v/v) or vehicle alone at 0.030 ml/g maternal body weight at 0900 on E8. Pretreatment with the study peptides was given 30 minutes prior to alcohol administration.

Treatment groups included: alcohol alone, to confirm the model; control to confirm that the dilutant/injection was not deleterious; pretreatment with NAPVSIPQ (SEQ ID NO:2) (20 $\mu$g) or SALLRSIPA (SEQ ID NO:1) (20 $\mu$g) to evaluate their efficacy in preventing FAS; pretreatment with VIP (1 $\mu$g); combination pretreatment with NAPVSIPQ (SEQ ID NO:2) (20 $\mu$g)+SALLRSIPA (SEQ ID NO:1) (20 $\mu$g) to evaluate if the combination of the two peptides is more efficacious in preventing FAS; pretreatment with NAPVSIPQ (SEQ ID NO:2) (40 $\mu$g) to determine if the efficacy seen with the combination of NAPVSIPQ (SEQ ID NO:2)+SALLRSIPA (SEQ ID NO:1) pretreatment is due to the increased dosage or an effect of the two different peptides; treatment with NAPVSIPQ (SEQ ID NO:2) (20 $\mu$g)+SALLRSIPA (SEQ ID NO:1) (20 $\mu$g) without alcohol to evaluate for toxicity of the peptides without the stress of alcohol.

To assess the protective effects of the ADNF peptides in the most severe form of stress, the number of fetal death was determined. On examination at E18, the total litter size (living fetuses+demises) was not different between the groups, with an average size of 8 fetuses. This documented that all litters began with the same number. The number of fetuses per treatment groups ranged between 120–280, with the litter mean used for analysis (litter numbers for each treatment are in FIG. Legend 1). The percentage of fetal demises was significantly higher in the alcohol than control group. (FIG. 1). Pretreatment with NAPVSIPQ (SEQ ID NO:2) or the combination of NAPVSIPQ (SEQ ID NO:2)+SALLRSIPA (SEQ ID NO:1) prevented the demises seen with alcohol, with levels significantly lower than the alcohol group (each $p<0.05$) and equivalent to the control group (FIG. 1). Pretreatment with SALLRSIPA (SEQ ID NO:1) alone was unable to bring the fetal demise rate to control levels. Pretreatment with VIP was given to assess its protective effects, and VIP slightly improved the fetal demise rate (FIG. 1). Treatment with NAPVSIPQ (SEQ ID NO:2)+SALLRSIPA (SEQ ID NO:1) without alcohol exposure did not alter the fetal demise percentage compared to control levels.

Figure 2A:
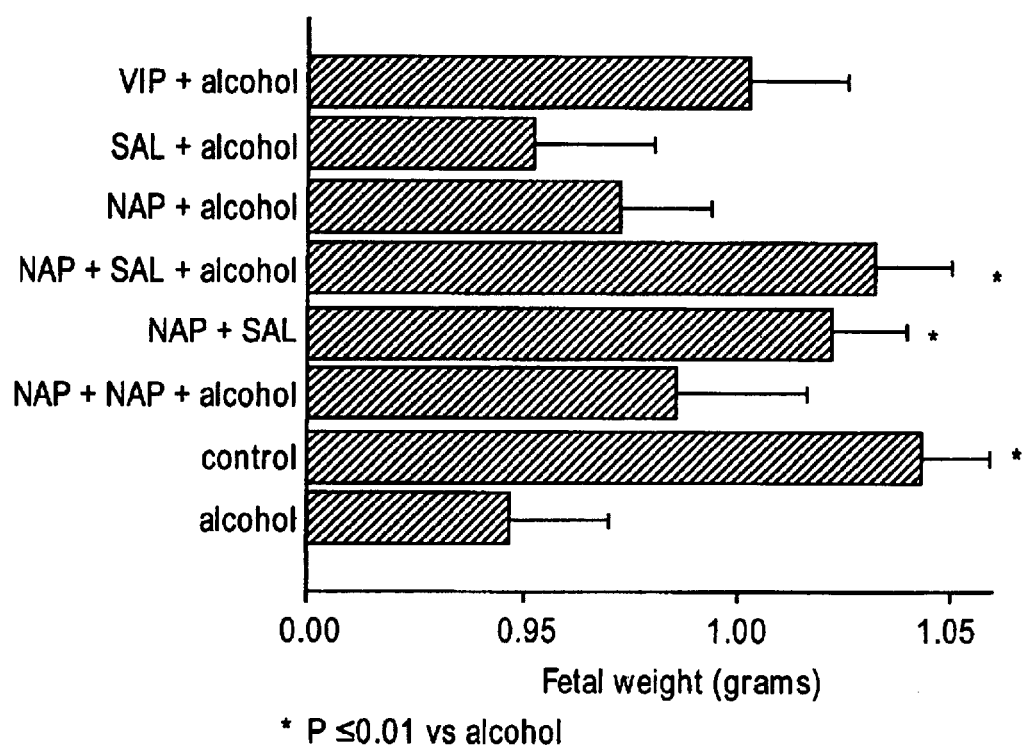
FIG. 2(A) and FIG. 2(B) illustrate the effects of pretreatment with ADNF polypeptides on fetal growth restriction and microcephaly. Fetal weights 2(A) and fetal brain weights 2(B) for each pregnant female were obtained at E18. Pretreatment with NAPVSIPQ (SEQ ID NQ:2)+ SALLRSIPA (SEQ ID NO:1) prevented the growth restriction associated with alcohol treatment. Comparisons are made to the alcohol group, overall ANOVA is p<0.001. Post-hoc Fishers tests were performed, with the * groups significantly different than the alcohol group. Sample size was the number of litters. The mean from each litter was used for statistical analysis and represents on average 8–10 fetuses. The sample sizes were control (32), alcohol (27), NAPVSIPQ (SEQ ID NO:2)+alcohol (24), NAPVSIPQ (SEQ ID NQ:2)+NAPVSIPQ (SEQ ID NO:2)+alcohol (17), SALLRSIPA (SEQ ID NO:1)+alcohol (11), VIP+alcohol (17), NAPVSIPQ (SEQ ID NO:2)+SALLRSIPA (SEQ ID NO:1)+alcohol (19), and NAPVSIPQ (SEQ ID NO:2)+ SALLRSIPA (SEQ ID NO:1) alone (19).
Figure 2B:
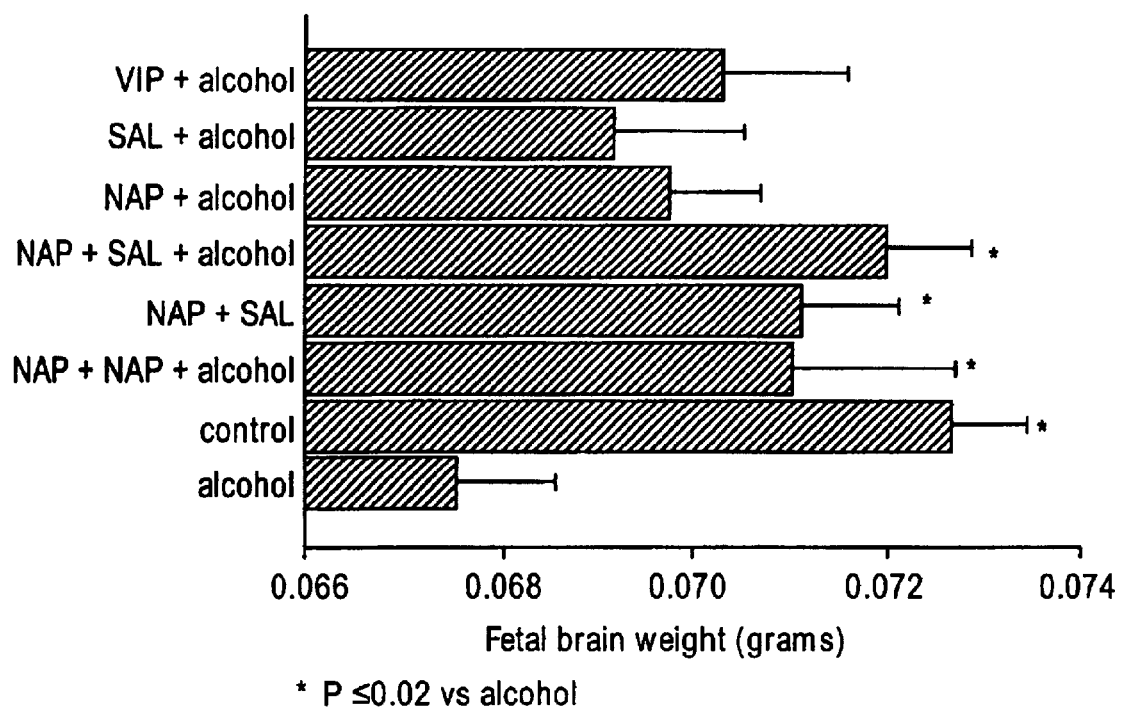

In the surviving E18 fetuses, fetal and fetal brain weights were evaluated to assess the protective effects of the ADNF peptides. Both fetal and fetal brain weights were significantly smaller in the alcohol treated group than in control or those pretreated with NAPVSIPQ (SEQ ID NO:2)+SALLRSIPA (SEQ ID NO:1) (FIGS. 2a, 2b). Pretreatment with NAPVSIPQ (SEQ ID NO:2) alone moderately prevented the alcohol-induced growth restrictions. Pretreatment with SALLRSIPA (SEQ ID NO:1) alone did not prevent the alcohol-induced fetal weight reduction, but moderately prevented the alcohol-induced fetal brain weight reduction. Similarly, pretreatment with a double dosage of NAPVSIPQ (SEQ ID NO:2) (40 $\mu$g) moderately prevented the alcohol-induced growth restriction, indicating that it is the combination of the two ADNF (ADNF I and ADNF III) peptides, rather than the dosage, required for the superior effect shown with a combination of NAPVSIPQ (SEQ ID NO:2)+SALLRSIPA (SEQ ID NO:1). Pretreatment with VIP improved embryonic weights; however, the effect was intermediate. NAPVSIPQ (SEQ ID NO:2)+SALLRSIPA (SEQ ID NO:1) treatment without alcohol exposure did not affect fetal weights. (FIGS. 2a, 2b).

VIP is known to have a temporal relationship in the embryo/decidua during gestation, with levels significantly higher at E9 than E17 (Spong et al., *Endocrinol* (In Press)). To evaluate the effect of alcohol exposure on VIP, VIP levels were measured in the embryo/decidua and maternal cortex at different time points (6 h, 24 h and 48 h) after treatment. Some samples had VIP levels below the ELISA's detection limits, therefore median values are presented. Embryo/decidual VIP levels were similar in control and alcohol groups 6 h after treatment. However, in the embryo/decidua at 24 h and 48 h, all VIP levels were below the ELISA's detection limit in the alcohol treated groups, and thus significantly lower than the control or NAPVSIPQ (SEQ ID NO:2)+SALLRSIPA (SEQ ID NO:1) pretreated groups at 24 h (0.6, 0.7) ng/10 $\mu$g protein, respectively) and 48 h (0.5, 0.6 ng/10 $\mu$g protein, respectively) ($p=0.001$). At both 6 and 24 hours after treatment, maternal cortex VIP levels were all undetectable and therefore significantly lower in the alcohol treated group than control or NAPVSIPQ (SEQ ID NO:2)+SALLRSIPA (SEQ ID NO:1) pretreatment ($p=0.0003$). At 48 h, the three groups had similar maternal cortex VIP levels [alcohol (1.0); control (1.2); NAPVSIPQ (SEQ ID NO:2)+SALLRSIPA (SEQ ID NO:1) pretreatment (1.0) ng/10 $\mu$g protein]. There appears to be a temporal relationship between maternal alcohol administration and VIP levels, with an initial decline in maternal levels at 6 h and 24 h and recovery by 48 h whereas in the embryo/decidua the levels are not affected until the significant decline at 24 and 48 hours.

Figure 3:
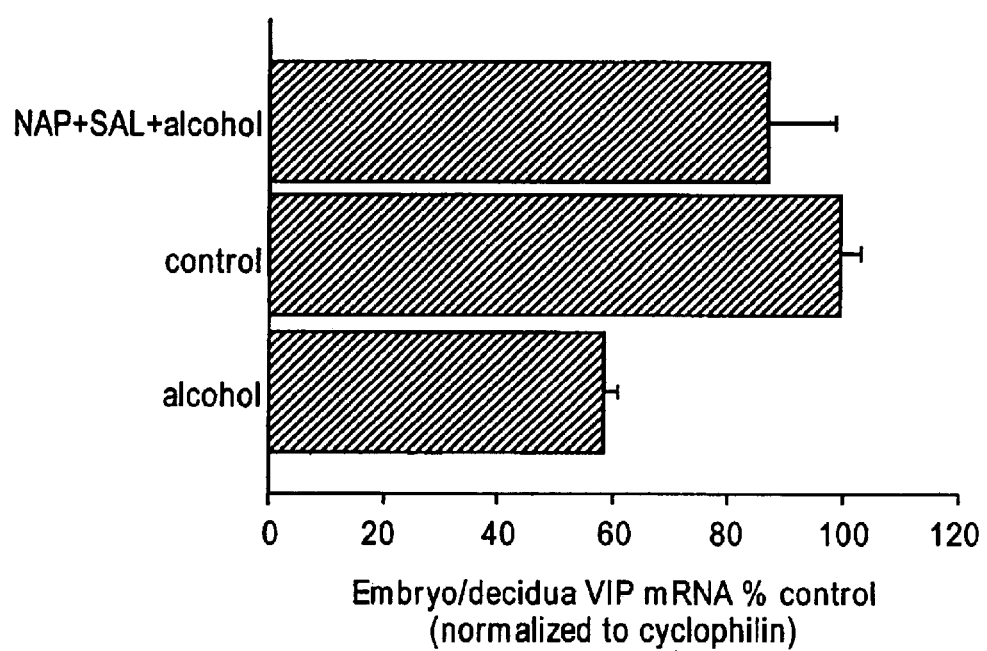
FIG. 3 illustrates the effect of ADNF polypeptides on the VIP mRNA level after alcohol treatment. VIP mRNA was quantitated in embryo/decidua 6 hours after treatment. Treatment groups were alcohol, control and NAPVSIPQ (SEQ ID NO:2)+SALLRSIPA (SEQ ID NO:1)+alcohol, with the NAPVSIPQ (SEQ ID NO:2)+SALLRSIPA (SEQ ID NO:1) given 30 min before alcohol. Embryo/decidual samples were pooled in groups of 3, at least three samples were run per treatment. Both VIP and cyclophilin mRNA were quantitated and the VIP mRNA was normalized to cyclophilin and expressed as the percentage of control values. Alcohol treatment significantly decreased VIP mRNA, whereas pretreatment with NAPVSIPQ (SEQ ID NO:2)+SALLRSIPA (SEQ ID NO:1) brought VIP mRNA levels back to control.

VIP mRNA also has a defined temporal relationship in early pregnancy with a significant increase in the decidua at E6-E8 compared to E17 (Spong et al., *Endocrinol.* (In Press)). Quantitative rt-PCR of the embryo/decidua demonstrated a significant decline in VIP mRNA levels 6 h after alcohol treatment, to 58% of control levels ($p<0.02$). (FIG. 3) However, pretreatment with NAPVSIPQ (SEQ ID NO:2)+SALLRSIPA (SEQ ID NO:1) increased VIP mRNA levels to those of controls (87%).

VIP binding sites were significantly increased to 25% greater than control in the decidua of the alcohol-treated embryos at 6 h and remained elevated at 24 and 48 h, indicating a long-lasting effect of alcohol-induced changes. Pre-treatment with NAPVSIPQ (SEQ ID NO:2)+SALLRSIPA (SEQ ID NO:1) had no effect on the alcohol-induced upregulation of VIP binding sites.

ADNF peptides, such as SALLRSIPA (SEQ ID NO:1) and NAPVSIPQ (SEQ ID NO:2), moderately prevented alcohol toxicity as measured by fetal demises and weight.

The combination of ADNF I and ADNF III peptides, e.g., NAPVSIPQ (SEQ ID NO:2)+SALLRSIPA (SEQ ID NO:1), showed the best results in terms of successful reversal of fetal demises and maintenance of weights (fetal and fetal brain). Without wishing to be bound by any theory, the effects of alcohol appear to be mediated through VIP or VIP effectors, with significant declines in VIP mRNA and peptide levels and increase in VIP binding sites after alcohol treatment. As expected, by giving alcohol to the mother, maternal VIP levels were the first to decline, followed by embryo/decidual levels. Pretreatment with the combination of ANDF peptides NAPVSIPQ (SEQ ID NO:2)+ SALLRSIPA (SEQ ID NO:1) prevented these declines in VIP.

What is claimed is:

1. A method for reducing a condition associated with fetal alcohol syndrome in a fetus who is exposed to alcohol in utero, the method comprising administering to the fetus while in utero an activity dependent neurotrophic factor (ADNF) polypeptide in an amount sufficient to reduce the condition associated with fetal alcohol syndrome;

wherein the ADNF polypeptide is administered before alcohol exposure;

wherein the condition associated with fetal alcohol syndrome is selected from the group consisting of decreased body weight of the fetus, decreased brain weight of the fetus, decreased level of vasoactive intestinal peptide (VIP) mRNA of the fetus, and likelihood of death of the fetus in utero; and wherein the ADNF polypeptide is a member selected from the group consisting of:

(a) an ADNF I polypeptide having the following amino acid sequence:

$(R^1)_x$-Ser-Ala-Leu-Leu-Arg-Ser-Ile-Pro-Ala-$(R^2)_y$ (SEQ ID NO:3);

(b) an ADNF III polypeptide having the following amino acid sequence:

$(R^3)_w$-Asn-Ala-Pro-Val-Ser-Ile-Pro-Gln-$(R^4)_z$ (SEQ ID NO:4);

(c) a mixture of the ADNF I polypeptide of part (a) and the ADNF III polypeptide of part (b);

wherein $R^1, R^2, R^3$, and $R^4$ are independently selected and are an amino acid sequence comprising from 1 to about 40 amino acids wherein each amino acid is independently selected; and x, y, w, and z are independently selected and are equal to zero or one.

2. The method of claim 1, wherein for the ADNF I polypeptide x and y are both zero.

3. The method of claim 1, wherein for the ADNF I polypeptide:

x is one;

$R^1$ is Val-Leu-Gly-Gly-Gly (SEQ ID NO:5); and y is zero.

4. The method of claim 1, wherein for the ADNF I polypeptide:

x is one;

R$^1$ is Val-Glu-Glu-Gly-Ile-Val-Leu-Gly-Gly-Gly (SEQ ID NO:6); and y is zero.

5. The method of claim 1, wherein for the ADNF III polypeptide w and z are both zero.

6. The method of claim 1, wherein for the ADNF III polypeptide:

w is one;

R$^3$ is Gly-Gly; and z is zero.

7. The method of claim 1, wherein for the ADNF III polypeptide:

w is one;

R$^3$ is Leu-Gly-Gly;

z is one; and

R$^4$ is Gln-Ser.

8. The method of claim 1, wherein for the ADNF III polypeptide:

w is one;

R$^3$ is Leu-Gly-Leu-Gly-Gly (SEQ ID NO:7);

z is one; and

R$^4$ is Gln-Ser.

9. The method of claim 1, wherein for the ADNF III polypeptide:

w is one;

R$^3$ is Ser-Val-Arg-Leu-Gly-Leu-Gly-Gly (SEQ ID NO:8);

z is one; and

R$^4$ is Gln-Ser.

10. The method of claim 1, wherein the ADNF polypeptide is a mixture of ADNF I polypeptide of part (a) and the ADNF III polypeptide of part (b).

11. The method of claim 1, wherein x, y, w, and z are all zero.

12. The method of claim 1, wherein the condition is a decreased body weight of the fetus.

13. The method of claim 1, wherein the condition is a decreased brain weight of the fetus.

14. The method of claim 1, wherein the condition is a decreased level of VIP mRNA of the fetus.

15. The method of claim 1, wherein the condition is likelihood of death of the fetus in utero.

16. The method of claim 1, wherein the ADNF polypeptide is a mixture of an ADNF I polypeptide consisting of SEQ ID NQ:1 and an ADNF III polypeptide consisting of SEQ ID NO:2.

* * * * *

SEQUENCE LISTING

```
<160> NUMBER OF SEQ ID NOS: 26

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:activity
      dependent neurotrophic factor I (ADNF I) active
      site

<400> SEQUENCE: 1

Ser Ala Leu Leu Arg Ser Ile Pro Ala
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:activity
      dependent neurotrophic factor III (ADNF III)
      active site

<400> SEQUENCE: 2

Asn Ala Pro Val Ser Ile Pro Gln
 1               5

<210> SEQ ID NO 3
<211> LENGTH: 89
<212> TYPE: PRT
<213> ORGANISM: Artificial Sequence
<220> FEATURE:
<223> OTHER INFORMATION: Description of Artificial Sequence:ADNF I
      polypeptide
<220> FEATURE:
<221> NAME/KEY: MOD_RES
<222> LOCATION: (1)..(40)
<223> OTHER INFORMATION: Xaa = any amino acid, Xaa at positions 1-40 may
      be present or absent
<220> FEATURE:
<221> NAME/KEY: MOD_RES
<222> LOCATION: (50)..(89)
<223> OTHER INFORMATION: Xaa = any amino acid, Xaa at positions 50-89
      may be present or absent

<400> SEQUENCE: 3

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Ser Ala Leu Leu Arg Ser Ile Pro
         35                  40                  45

Ala Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80
```

```
Xaa Xaa Xaa Xaa Xaa Xaa Xaa Xaa Xaa
            85

<210> SEQ ID NO 4
<211> LENGTH: 88
<212> TYPE: PRT
<213> ORGANISM: Artificial Sequence
<220> FEATURE:
<223> OTHER INFORMATION: Description of Artificial Sequence:ADNF I
      polypeptide
<220> FEATURE:
<221> NAME/KEY: MOD_RES
<222> LOCATION: (1)..(40)
<223> OTHER INFORMATION: Xaa = any amino acid, Xaa at positions 1-40 may
      be present or absent
<220> FEATURE:
<221> NAME/KEY: MOD_RES
<222> LOCATION: (49)..(88)
<223> OTHER INFORMATION: Xaa = any amino acid, Xaa at positions 49-88
      may be present or absent

<400> SEQUENCE: 4

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Ala Pro Val Ser Ile Pro Gln
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa
            85

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:1-R or 2-R
      in ADNF I polypeptide formula

<400> SEQUENCE: 5

Val Leu Gly Gly Gly
 1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence:1-R in ADNF
      I polypeptide formula

<400> SEQUENCE: 6

Val Glu Glu Gly Ile Val Leu Gly Gly Gly
 1               5                  10

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:3-R or 4-R
      in ADNF III polypeptide formula
```

```
<400> SEQUENCE: 7

Leu Gly Leu Gly Gly
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence:3-R  in ADNF
      III polypeptide formula

<400> SEQUENCE: 8

Ser Val Arg Gly Leu Gly Gly
  1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:2-R in ADNF
      I polypeptide formula

<400> SEQUENCE: 9

Val Leu Gly Gly
  1

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence:2-R in ADNF
      I polypeptide formula

<400> SEQUENCE: 10

Val Leu Gly Gly Val
  1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:2-R in ADNF
      I polypeptide formula

<400> SEQUENCE: 11

Gly Val Leu Gly Gly
  1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence:4-R in ADNF
      III polypeptide formula

<400> SEQUENCE: 12

Leu Gly Leu Gly
  1

<210> SEQ ID NO 13
<211> LENGTH: 5
```

```
<212> TYPE: PRT
<213> ORGANISM: Artificial Sequence
<220> FEATURE:
<223> OTHER INFORMATION: Description of Artificial Sequence:4-R in ADNF
      III polypeptide formula

<400> SEQUENCE: 13

Leu Gly Leu Gly Leu
 1               5

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 14

Val Leu Gly Gly Gly Ser Ala Leu Leu Arg Ser Ile Pro Ala Val Leu
 1               5                  10                  15

Gly Gly Gly

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 15

Val Leu Gly Gly Gly Ser Ala Leu Leu Arg Ser Ile Pro Ala Val Leu
 1               5                  10                  15

Gly Gly

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 16

Val Leu Gly Gly Gly Ser Ala Leu Leu Arg Ser Ile Pro Ala Val Leu
 1               5                  10                  15

Gly Gly Val

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 17

Val Leu Gly Gly Gly Ser Ala Leu Leu Arg Ser Ile Pro Ala Gly Val
 1               5                  10                  15

Leu Gly Gly

<210> SEQ ID NO 18
<211> LENGTH: 18
<212> TYPE: PRT
```

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 18

Leu Gly Leu Gly Gly Asn Ala Pro Val Ser Ile Pro Gln Leu Gly Leu
 1               5                  10                  15
Gly Gly

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 19

Leu Gly Leu Gly Gly Asn Ala Pro Val Ser Ile Pro Gln Leu Gly Leu
 1               5                  10                  15
Gly

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 20

Leu Gly Leu Gly Gly Asn Ala Pro Val Ser Ile Pro Gln Leu Gly Leu
 1               5                  10                  15
Gly Leu

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 21

Val Leu Gly Gly Gly Ser Ala Leu Leu Arg Ser Ile Pro Ala
 1               5                  10

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 22

Val Glu Glu Gly Ile Val Leu Gly Gly Gly Ser Ala Leu Leu Arg Ser
 1               5                  10                  15
Ile Pro Ala

<210> SEQ ID NO 23
<211> LENGTH: 10
<212> TYPE: PRT
<213> ORGANISM: Artificial Sequence -continued

```
<220> FEATURE:
<223> OTHER INFORMATION: Description of Artificial Sequence:ADNF III
      polypeptide

<400> SEQUENCE: 23

Gly Gly Asn Ala Pro Val Ser Ile Pro Gln
  1               5                  10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 24

Leu Gly Gly Asn Ala Pro Val Ser Ile Pro Gln Gln Ser
  1               5                  10

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 25

Leu Gly Leu Gly Gly Asn Ala Pro Val Ser Ile Pro Gln Gln Ser
  1               5                  10                  15

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 26

Ser Val Arg Gly Leu Gly Gly Asn Ala Pro Val Ser Ile Pro Gln Gln
  1               5                  10                  15

Ser
```